US012571398B2

(12) United States Patent
Du et al.

(10) Patent No.: US 12,571,398 B2
(45) Date of Patent: Mar. 10, 2026

(54) FAN FOR AN AUTOMATIC DISPENSING DEVICE

(71) Applicant: Reckitt & Colman (Overseas) Hygiene Home Limited, Slough (GB)

(72) Inventors: Lavis Du, Shenzhen (CN); Chaoqin Guo, Guangdong (CN); Dan Ibbitson, Hull (GB); Akira Naidu, Liverpool (GB); Jake Stephen Williams, Hull (GB); Charles Yao, Shenzhen (CN)

(73) Assignee: Reckitt & Colman (Overseas) Hygiene Home Limited, Slough (GB)

( * ) Notice: Subject to any disclaimer, the term of this patent is extended or adjusted under 35 U.S.C. 154(b) by 0 days.

(21) Appl. No.: 18/867,119

(22) PCT Filed: May 18, 2023

(86) PCT No.: PCT/GB2023/051307
§ 371 (c)(1),
(2) Date: Nov. 19, 2024

(87) PCT Pub. No.: WO2023/227866
PCT Pub. Date: Nov. 30, 2023

(65) Prior Publication Data
US 2025/0207601 A1 Jun. 26, 2025

(30) Foreign Application Priority Data

May 23, 2022 (WO) ................ PCT/CN2022/094437
Jun. 29, 2022 (GB) ..................................... 2209510

(51) Int. Cl.
*F04D 25/06* (2006.01)
*A61L 9/12* (2006.01)
(Continued)

(52) U.S. Cl.
CPC .............. *F04D 25/06* (2013.01); *A61L 9/122* (2013.01); *H02K 11/33* (2016.01); *F04D 25/0653* (2013.01); *H02K 1/2795* (2022.01)

(58) Field of Classification Search
CPC .......................... F04D 25/0653; H02K 1/2795
(Continued)

(56) References Cited

U.S. PATENT DOCUMENTS 4,504,751 A * 3/1985 Meier .................... H02K 29/08
416/93 R
4,725,752 A * 2/1988 Shiraki .................. H02K 29/08
310/156.32
(Continued)

FOREIGN PATENT DOCUMENTS

CN 206329513 U 7/2017
CN 215934536 U 3/2022
(Continued)

OTHER PUBLICATIONS

International Search Report and Written Opinion of the International Searching Authority for corresponding application PCT/GB2023/051307 dated Aug. 2, 2023.
(Continued)

*Primary Examiner* — Thomas Fink
(74) *Attorney, Agent, or Firm* — Norris McLaughlin, PA

(57) ABSTRACT

A fan (1) for an automatic dispensing device, wherein the fan (1) is configured to generate an air flow when a rotor (3) of the fan (1) is rotating. The fan (1) comprises a drive circuit (6), an electromagnet (8) having at least one electromagnetic coil, the electromagnetic coil connected to the drive circuit (6), a rotor (3) for generating the airflow, and at least four magnets (14a, 14b, 14c, 14d, 14e, 14f, 14g, 14h) arranged on a circle (18) on the rotor (3) and spaced apart by the same angle (alpha), wherein the electromagnet (8) is
(Continued)

arranged above or under the circle (18) of the rotor (3) and configured to attract or repel said magnets (14a, 14b, 14c, 14d, 14e, 14f, 14g, 14h), and the drive circuit (6) is configured to switch a current direction in the electromagnetic coil of the electromagnet (8) to sequentially attract and then repel each magnet as the rotor rotates. The fan further comprises a magnetic element (16) arranged above or under the rotor (3) in proximity (20) of the circle (18) of the rotor (3) such that the magnetic element (16) attracts one of the magnets (14a) to its position when the electromagnetic coil is not powered by the drive circuit (6) and the rotor (3) is not rotating or gradually coming to a halt after the electromagnetic coil has been un-powered, wherein none of the other magnets (14b, 14c, 14d, 14e, 14f, 14g, 14h) assumes a position directly under or above the electromagnet (8) when the rotor (3) comes to a halt. In a preferred embodiment, the fan (1) further includes a "floating suspension" to reduce wear and tear over time.

16 Claims, 8 Drawing Sheets

(51) Int. Cl.
   *H02K 11/33*            (2016.01)
   *H02K 1/2795*          (2022.01)
(58) Field of Classification Search
   USPC ...................................................... 310/49.55
   See application file for complete search history.

(56)                    References Cited

U.S. PATENT DOCUMENTS

| | | | |
|---|---|---|---|
| 4,728,833 A * | 3/1988 | Shiraki ................. | H02K 29/08 |
| | | | 310/43 |
| 4,733,119 A * | 3/1988 | Shiraki ................. | H02K 29/08 |
| | | | 310/68 R |
| 4,894,572 A * | 1/1990 | Shiraki ................. | H02K 29/03 |
| | | | 310/179 |
| 2007/0176508 A1* | 8/2007 | Kasai ..................... | H02K 29/08 |
| | | | 310/156.32 |
| 2008/0018187 A1* | 1/2008 | Yamaguchi ........... | H02K 1/182 |
| | | | 310/71 |
| 2008/0152482 A1* | 6/2008 | Patel ..................... | F04D 25/084 |
| | | | 415/121.3 |
| 2009/0175744 A1 | 7/2009 | Horing et al. | |
| 2011/0148226 A1* | 6/2011 | Horng ................... | H02K 21/24 |
| | | | 310/156.43 |
| 2014/0203680 A1 | 7/2014 | Yin et al. | |
| 2014/0232246 A1* | 8/2014 | Sugiura ................. | H02K 5/15 |
| | | | 310/90 |

FOREIGN PATENT DOCUMENTS

| | | | |
|---|---|---|---|
| EP | 2955840 | A1 | 12/2015 |
| GB | 2589623 | A | 6/2021 |
| JP | 2015104593 | A | 6/2015 |
| WO | 2021111146 | A1 | 6/2021 |

OTHER PUBLICATIONS

GB Search Report for corresponding application GB 2209510.3 dated Dec. 1, 2022.

* cited by examiner

FAN FOR AN AUTOMATIC DISPENSING DEVICE

This is an application filed under 35 USC 371 based on PCT/GB2023/051307 (WO 2023/227866) filed 18 May 2023, which claimed priority to PCT/CN2022/094437 filed 23 May 2022, and to GB 2209510.3 filed 29 Jun. 2022. The present application claims the full priority benefit of all prior applications and incorporates by reference their full disclosures as if set forth herein.

The present disclosure relates to a fan, for example for an automatic dispensing device. The fan can be used to generate an airflow for emanating a volatile substance which may include e.g. an air freshener or insecticides.

In general, the rate at which automatic dispensing devices emit volatile substances can be altered by changing the airflow. For example, a motion of a fan element can be used to increase the flow of volatile substances and increase distribution of the volatile substance. It is also beneficial to increase airflow away from the dispensing device so that the volatile substance is distributed more widely and further from the dispensing device.

The increased airflow can be energy intensive. Effective distribution of a volatile substance can lead to high battery capacity requirement which can lead to difficulty using renewable energy as a provision of power. The fan described in the present disclosure provides a more efficient driving mechanism to generate airflow that allows volatile substances to be distributed using a lower energy requirement.

WO2021/111146 discloses a dispensing device with an efficient fan drive.

It is an object of the present invention to further improve the efficiency of the fan, e.g. for an automatic dispenser.

This objective is achieved by a fan incorporating the features of independent claim 1. Preferred embodiments are laid out in the dependent claims.

In the following, the prior art as well as the present invention are illustrated with reference to the figures.

Figure 1:
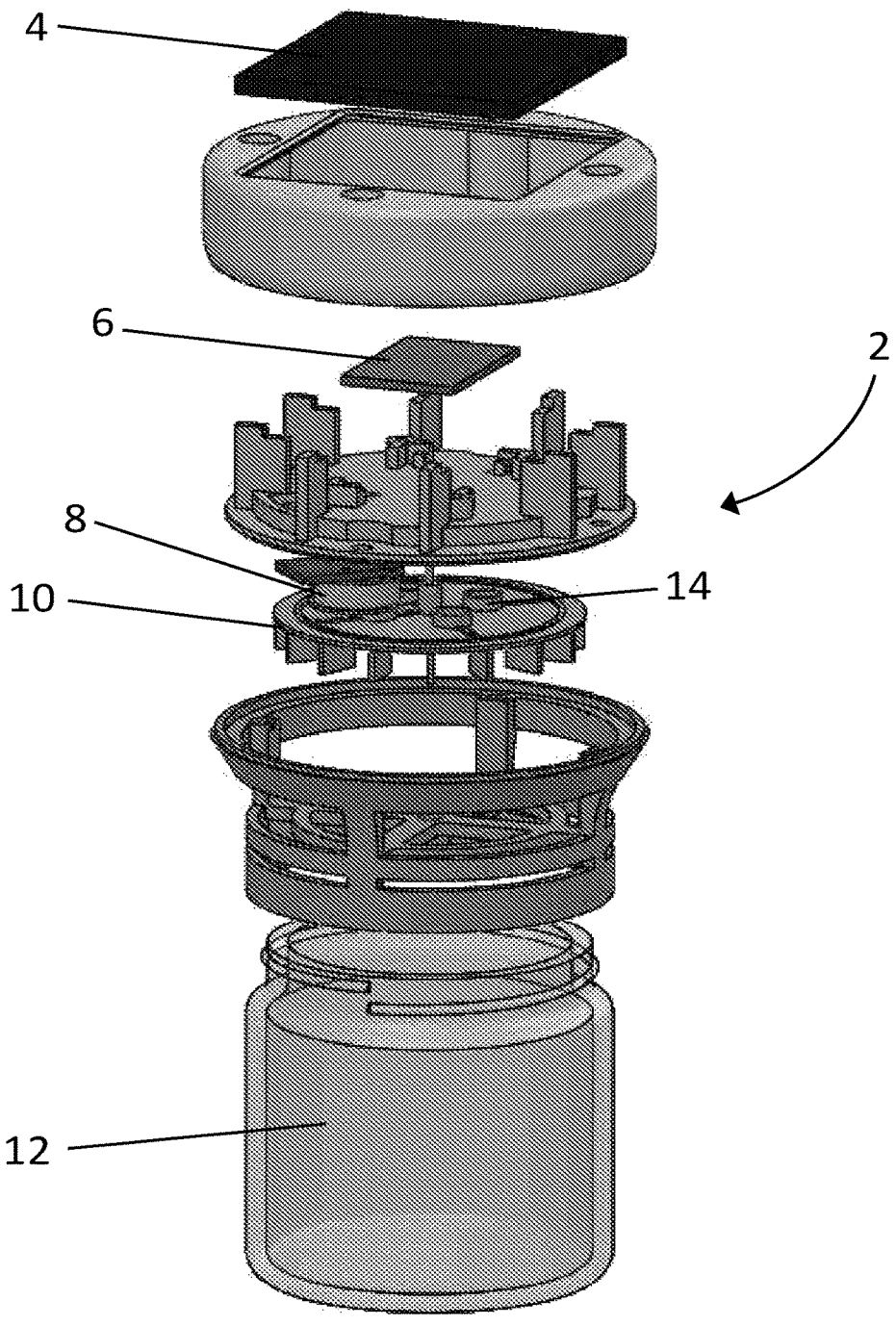
FIG. 1 shows a schematic illustration of an automatic dispensing device according to the prior art.

FIG. 1 shows an example of an automatic dispensing device 2. The automatic dispensing device 2 of FIG. 1 comprises a solar panel 4, a drive circuit 6, an electromagnet 8, a fan 10, at least one magnet 14 and a reservoir 12 containing a volatile substance.

The solar panel 4 is coupled to the drive circuit 6 which is connected to the electromagnet 8. The fan 10 is coupled to the at least one magnet 14. The fan 10 is located proximate to the electromagnet 8 so that the magnetic field generated by the electromagnet is sufficiently strong to attract or repel the at least one magnet 14. The fan 10 is located proximate to the reservoir 12 so that the fan increases airflow and distribution of the volatile substance is increased.

In the example illustrated in FIG. 1, the drive circuit is configured to receive power from the solar panel 4. The power received by the from the solar panel may be stored by the drive circuit using, for example, a battery. The power received from the solar panel 4 is used to drive the electromagnet 8 and the current driven through the electromagnet generates a magnetic field. The magnetic field can be altered by varying the magnitude and direction of the current. For example, the poles of the electromagnet 8 may be switched by changing the direction of the current.

Figure 2:
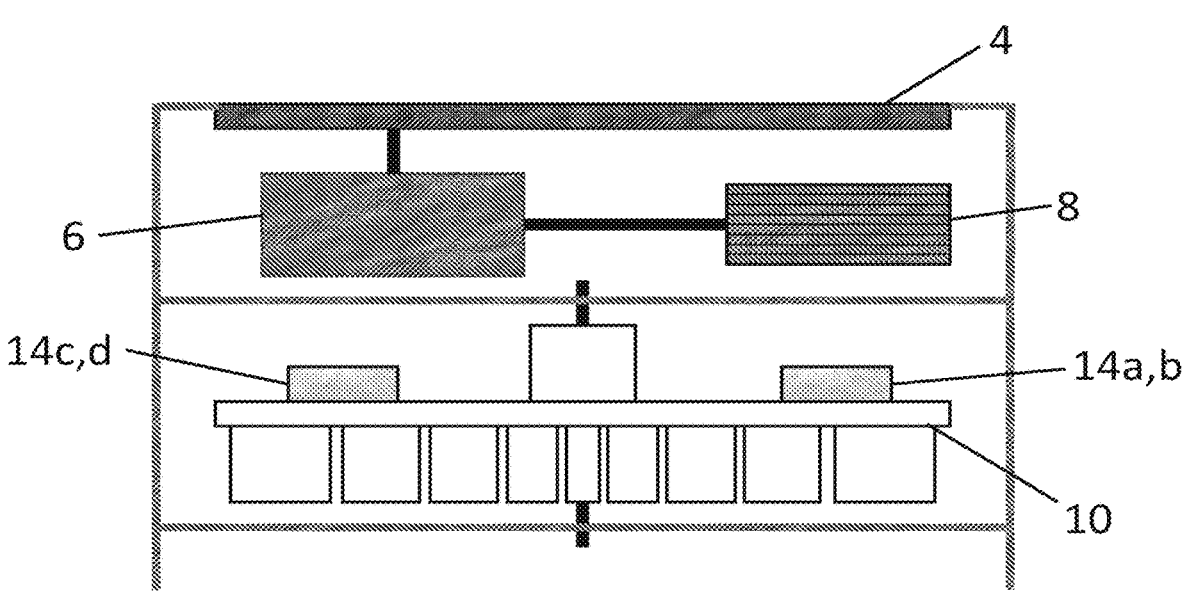
FIG. 2 shows an illustration of the components of the automatic dispensing device of FIG. 1 (prior art)

FIG. 2 shows an example of a drive mechanism that may be used with the device of FIG. 1. The illustration in FIG. 2 shows the solar panel 4 connected to the drive circuit 6 which in turn is connected to the electromagnet 8. In the example illustrated in FIG. 2, the electromagnet 8 is positioned above the one of the at least one magnet 14 that is attached to the fan 10. In the example illustrated in FIG. 2 there are 4 magnets 14a,b,c,d attached to the fan.

Figure 3:
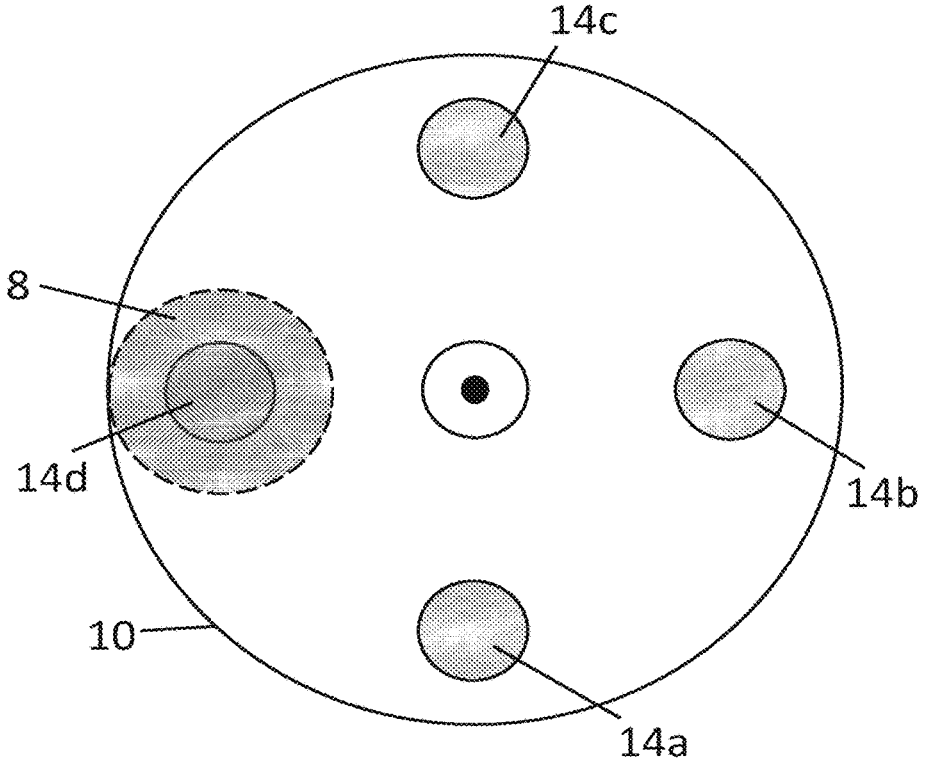
FIG. 3 is a top view of the automatic dispensing device showing the fan and drive mechanism according to the prior art.

FIG. 3 shows a top view of the drive mechanism of FIG. 2. This top view shows the relative position of the electromagnet 8, the magnets 14a,b,c,d and fan 10. In the example illustrated in FIGS. 2 and 3, the magnets on the fan are located at equidistance from one another i.e. located at 90-degree intervals on the top surface of the fan. In this example, the pole of each magnet is oriented in the same direction. For example, north-north-north-north or south-south-south-south.

Figure 4:
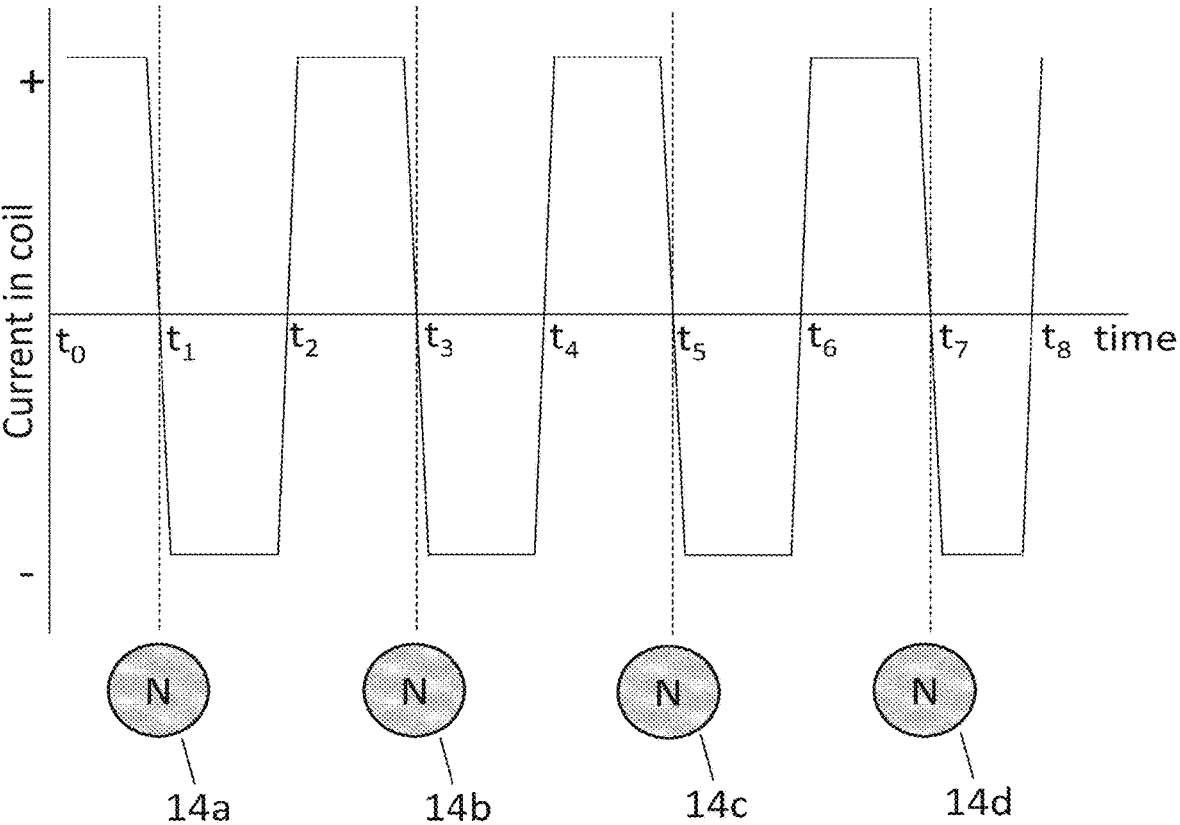
FIG. 4 shows an example of how the current is varied through an electromagnet to drive the fan of the automatic dispensing device according to the prior art.

FIG. 4 shows a graphical illustration how the current may be varied through the electromagnet 8 and the position of the four magnets relative to the electromagnet in time. As illustrated, the current in the electromagnet is varied in time and switches from a positive current to a negative current or from a negative current to a positive current as each magnet 14a,b,c,d passes the electromagnet and when equidistance between two magnets e.g. equidistance from magnet 14a and magnet 14b.

In this example, in order to generate the north pole and south pole from the electromagnet, the electromagnet comprises a coil that is wound such that a positive current generates a south pole and a negative current generates a north pole. The electromagnet is positioned proximate the magnets so that the magnetic energy is converted to kinetic energy in the fan via the magnetic interaction between the electromagnet 8 and the magnets 14a,b,c,d.

As shown in FIG. 4, at time to the electromagnet has a positive current and attracts magnet 14a. At time $t_1$ the magnet 14a passes the coil. The current through the electromagnet is switched to a negative current so that the electromagnet repels magnet 14a. At time $t_2$, the electromagnet is equidistance from magnet 14a and magnet 14b and the current in the electromagnet switches from negative to positive so that magnet 14b is attracted to the electromagnet. At time $t_3$ the magnet 14b passes the coil. The current through the electromagnet is switched to a negative current so that the electromagnet repels magnet 14b. At time $t_4$, the electromagnet is equidistance from magnet 14b and magnet 14c and the current in the electromagnet switches from negative to positive so that magnet 14c is attracted to the electromagnet. At time $t_5$ the magnet 14*c* passes the coil. The current through the electromagnet is switched to a negative current so that the electromagnet repels magnet 14*c*. At time $t_6$, the electromagnet is equidistance from magnet 14*c* and magnet 14*d* and the current in the electromagnet switches from negative to positive so that magnet 14*d* is attracted to the electromagnet. At time $t_7$ the magnet 14*d* passes the coil. The current through the electromagnet is switched to a negative current so that the electromagnet repels magnet 14*d*. At time $t_8$, the electromagnet is equidistance from magnet 14*d* and magnet 14*a* and the current in the electromagnet switches from negative to positive so that magnet 14*a* is attracted to the electromagnet.

The switching of the current in the electromagnet described above provides an efficient mechanism of transferring the electrical energy to kinetic energy in the fan using the magnetic attraction and repulsion between the electromagnet 8 and the magnets 14 coupled to the fan 10.

The circuit may be selected to provide an oscillating current on the electromagnet. In the example illustrated above the electromagnet comprises a single coil and the circuit selected in order to provide an oscillating current. The circuit may, for example, be a Schmitt trigger that provides an oscillating current to the coil. In other examples, a physical switch may be used to switch the current direction. In a further example, a logic integrated circuit (IC) may be used.

In another example, the electromagnet comprises a first coil 8*a* and a second coil 8*b*. The first coil 8*a* is located proximate to the second coil 8*b*. In this example, the fan is driven by the electromagnetic by applying a current in one direction through the first coil 8*a* and applying a current in the opposite direction in the second coil 8*b*. This results in the first coil 8*a* having a magnetic pole direction in the opposite direct to the magnetic pole from the second coil 8*b*.

Figure 5:
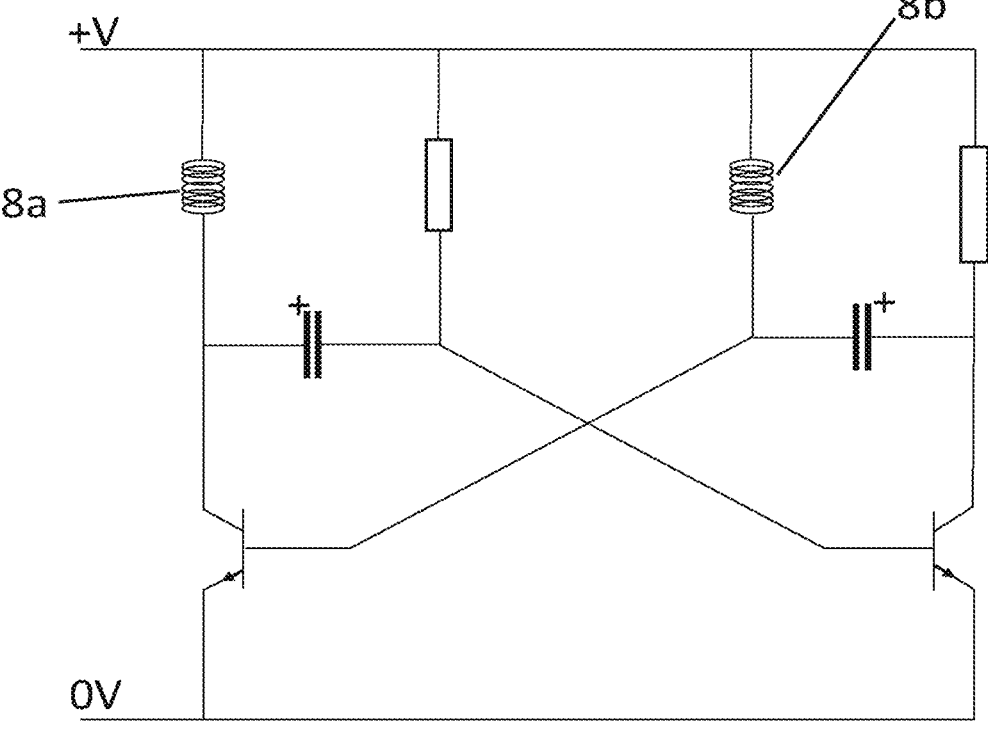
FIG. 5 is an example of a circuit that may be used to drive the fan element of the automatic dispensing device according to the prior art.

FIG. 5 shows an example of a circuit that may be used to provide a current that oscillate between passing current through first coil 8*a* and second coil 8*b*. In this example, the first coil 8*a* and second coil 8*b* are connected in the circuit so that the direction of the current in the first coil 8*a* is in the opposite direction to the current in the second coil 8*b*.

In the example described above the fan comprises four magnets 14. In other examples the fan may comprise a different number of magnets 14. For example, the fan may comprise 2, 3, 4, 6, 7 or 8 magnets. The number of magnets 14 may depend upon the size of the fan 10, for example it may be beneficial to use a greater number of magnets 14 for a larger fan 10.

Figure 6:
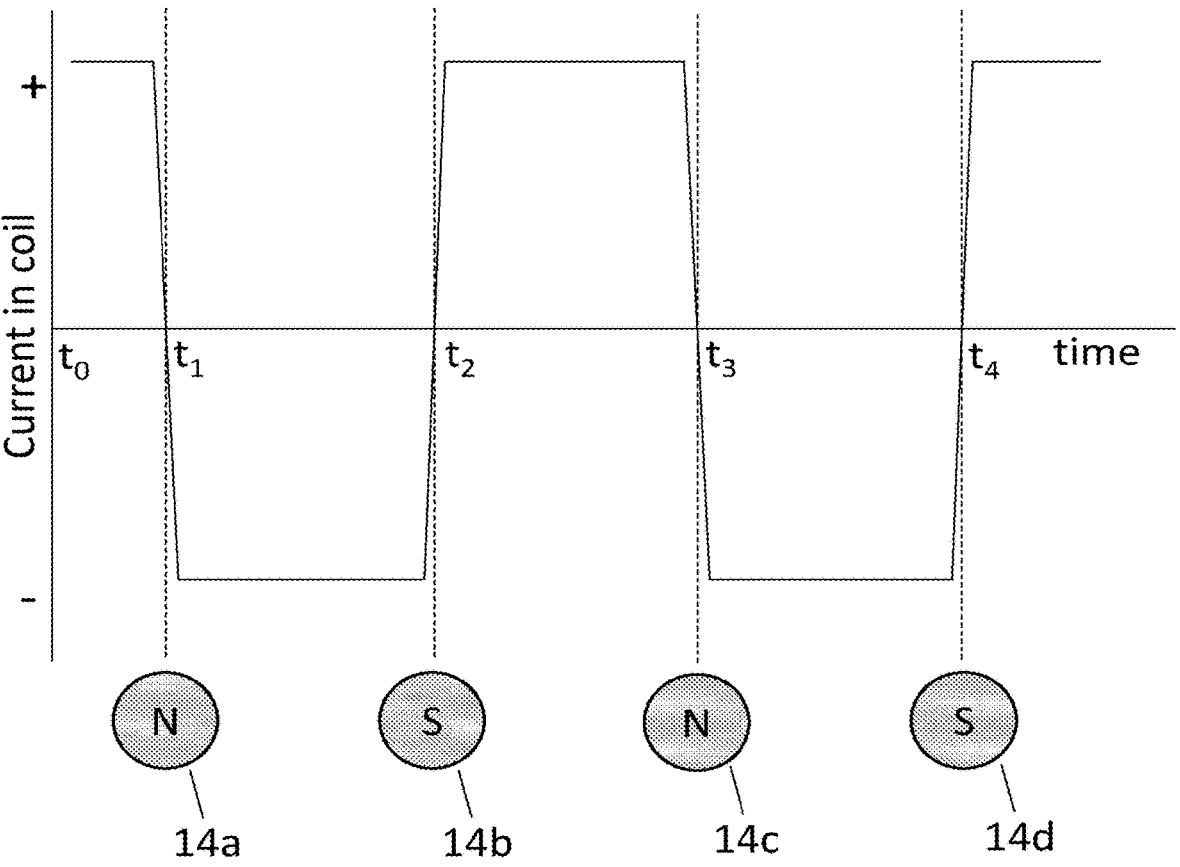
FIG. 6 shows a further example of how the current is varied through an electromagnet to drive the fan of the automatic dispensing device according to the prior art.

FIG. 6 represents an alternative arrangement where the poles of the magnets alternate. In this example, the pole of the magnet would be oriented so that the pole of each magnet facing the top surface alternates along the arc of fan i.e. successive magnets in a clockwise direction on the fan would have their poles in opposite directions. In the example where 4 magnets are located on the fan, the magnets are arranged to be north-south-north-south.

The graphical representation shows how the current may be varied through the electromagnet 8 and the position of the four magnets relative to the electromagnet in time. As illustrated, the current in the electromagnet is varied in time and switches from a positive current to a negative current or from a negative current to a positive current as each magnet 14*a,b,c,d* passes the electromagnet. In this example, in order to generate the north pole and south pole from the electromagnet, the electromagnet comprises a coil that is wound such that a positive current generates a south pole and a negative current generates a north pole. The electromagnet is positioned proximate the magnets so that the magnetic energy is converted to kinetic energy in the fan via the magnetic interaction between the electromagnet 8 and the magnets 14*a,b,c,d*.

As shown in FIG. 6, at time to the electromagnet has a positive current and attracts magnet 14*a*. At time $t_1$ the magnet 14*a* passes the coil. The current through the electromagnet is switched to a negative current so that the electromagnet repels magnet 14*a* and attracts magnet 14*b*. At time $t_2$, the electromagnet is switched to a positive current to repel magnet 14*b* and attract magnet 14*c*. At time $t_3$, the current in the electromagnet is once again reversed to be negative and repels magnet 14*c* and attracts magnet 14*d*. At time $t_4$, the current in the electromagnet is switched to be positive to repel magnet 14*d* and attract magnet 14*a*.

In the example above the magnet 14 is a neodymium magnet. In other examples, the one or more magnet may be a ferrite magnet and/or other rare earth magnet.

The electromagnet may be a coil made from copper, for example enamelled copper coil wire. In an example, the copper wire may have a thickness between 0.04 and 0.05 mm. In an example, the electromagnet may have between 1000 and 8000 turns on the coil, for example 2000 to 7000 turns, for example 3000 to 6000 turns, for example 4000 to 5000 turns.

In the example above, the automatic dispensing device comprises a solar panel. In other examples, the dispensing device may be powered from a power storage unit (e.g. battery power) and/or connected to an external electricity supply (e.g. mains power).

In the examples described above, the electromagnet 8 interacts with at least one magnet 14 coupled to the fan 10. The electromagnet 8 may also interact with at least one magnet 14 coupled to a paddle or stirrer that is configured to move within the volatile substance to generate a current in the volatile substance.

Any feature as described and depicted in the prior art as referred to above in FIGS. 1-6 can be used in combination with the fan of the present invention as e.g. depicted in the following FIGS. 7 and 8.

Figure 7:
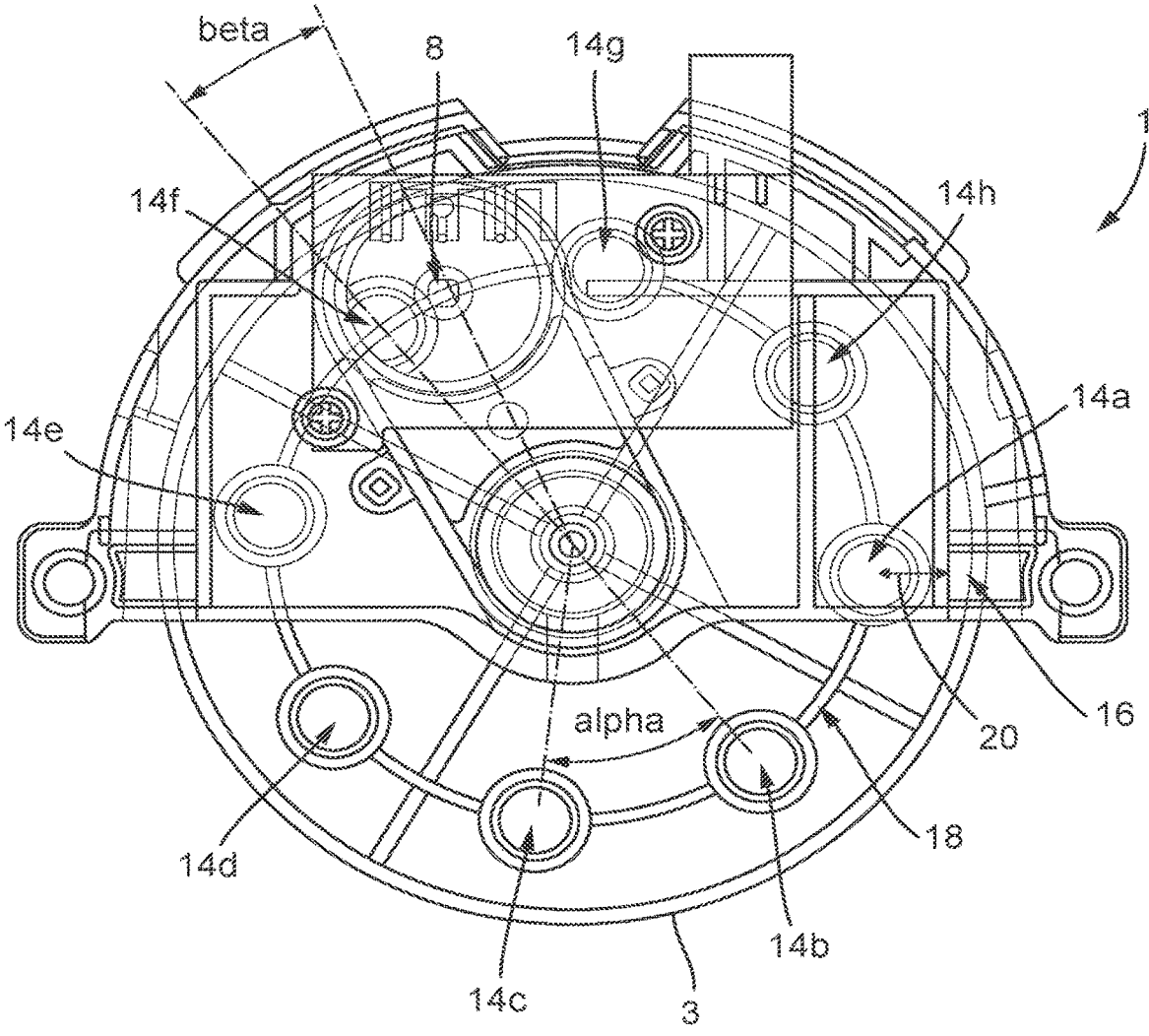
FIG. 7 shows an embodiment of the fan of the present invention.

FIG. 7 depicts a top view on a fan according to the present invention. The fan 1 includes a rotor 3. On the rotor 3, eight permanent magnets 14*a*, 14*b*, 14*c*, 14*d*, 14*e*, 14*f*, 14*g* and 14*h* are arranged on a circle 18 and spaced apart by 45 degrees. The fan blades for generating an airflow are arranged on the bottom side of the rotor (not shown here). The fan 1 includes an electromagnet 8 which has at least one electromagnetic coil. Here, the electromagnet 8 is arranged above the rotor 3. A drive circuit (not shown here, but see e.g. reference sign 6 in FIGS. 1 and 2) is connected to the electromagnetic coil of the electromagnet 8. The drive circuit is configured to switch a current direction in the electromagnetic coil of the electromagnet 8 to sequentially attract and then repel each magnet 14*a*, 14*b*, 14*c*, 14*d*, 14*e*, 14*f*, 14*g*, 14*h* as the rotor 3 rotates. A magnetic element 16 is arranged above the rotor in proximity 20 of the circle 18 of the rotor 3 such that the magnetic element 16 attracts one of the magnets 14*a* to its position when the electromagnetic coil is not powered by the drive circuit 6 and the rotor 3 is not rotating or gradually coming to a halt after the electromagnetic coil has been un-powered. In such situation, none of the other magnets 14*b*, 14*c*, 14*d*, 14*e*, 14*f*, 14*g*, 14*h* assumes a position directly under the electromagnetic coil of the electromagnet 8. In other words, the magnetic element 16 is configured to attract one of the at least four magnets 14*a* such that the one of the at least four magnets 14*a* intersects a radial line from the centre of the circle 18 of the rotor 3 and the magnetic element 16, wherein the at least four magnets 14a, 14b, 14c, 14d, 14e, 14f, 14g, 14h and the electromagnetic coil of the electromagnet 8 are arranged so that the at least four magnets 14a, 14b, 14c, 14d, 14e, 14f, 14g, 14h and the electromagnetic coil of the electromagnet 8 are misaligned when the magnet 14a intersects the radial line from the centre of the circle 18 of the rotor 3 and the magnetic element 16.

The magnetic element 16 can e.g. be an iron plate. Every time the rotor 3 of the fan 1 comes to a stop, the attractive force of the iron plate on the magnets ensures that one of the magnets 14a is attracted to its position and sits underneath it when the rotor 3 stops. The design of the fan 1, specifically the arrangement of the magnets and the electromagnetic coil of the electromagnet, ensures that one of the magnets 14b, 14c, 14d, 14e, 14f, 14g, 14h always stays at a fixed distance from the electromagnetic coil of the electromagnet 8 in said "stop" position of the rotor 3. This reduces the energy required to build momentum for the rotor of the fan to rotate upon activation. If a solar panel is used to power the fan, less light intensity (lux) is needed to activate the fan 1 compared to the prior art fan as depicted e.g. in FIGS. 1, 2 and 3.

TABLE 1

|  | Without iron plate 16: Startup-Lux | With iron plate 16: Startup-Lux |
| --- | --- | --- |
|  | 146 | 78 |
|  | 182 | 97 |
|  | 164 | 89 |
|  | 164 | 93 |
|  | 141 | 78 |
| average lux: | 159 | 87 |

Table 1 shows the lux data measured for activating (i.e. getting the rotor of the fan in motion) solar-powered fans. Five fans have been built according to the present invention (i.e. including the magnetic element 16; see FIG. 7), five are missing said feature. It can be seen that a considerably lower average light intensity (lux) is needed to activate a fan according to the invention. This also has the advantage that a fan according to the invention can be operated in dimmer light conditions—thus increasing the range of light conditions under which such solar-powered fan can be operated. It is also possible for the magnetic element 16 to include an active element such as an electromagnet which is e.g. briefly activated when the fan 1 is coming to a halt, to attract said one of magnets 14a to its position. The strength of magnetic attraction between the magnetic element 16 (e.g. iron plate) and said one of magnets 14a is weak, i.e. (considerably) weaker than between the electromagnet 8 and the magnets 14a, 14b, 14c, 14d, 14e, 14f, 14g, 14h such that the magnetic element 16 only has a minimal effect on the interaction between the electromagnet 8 and the magnets 14a, 14b, 14c, 14d, 14e, 14f, 14g, 14h during rotation of the fan 1.

Figure 8:
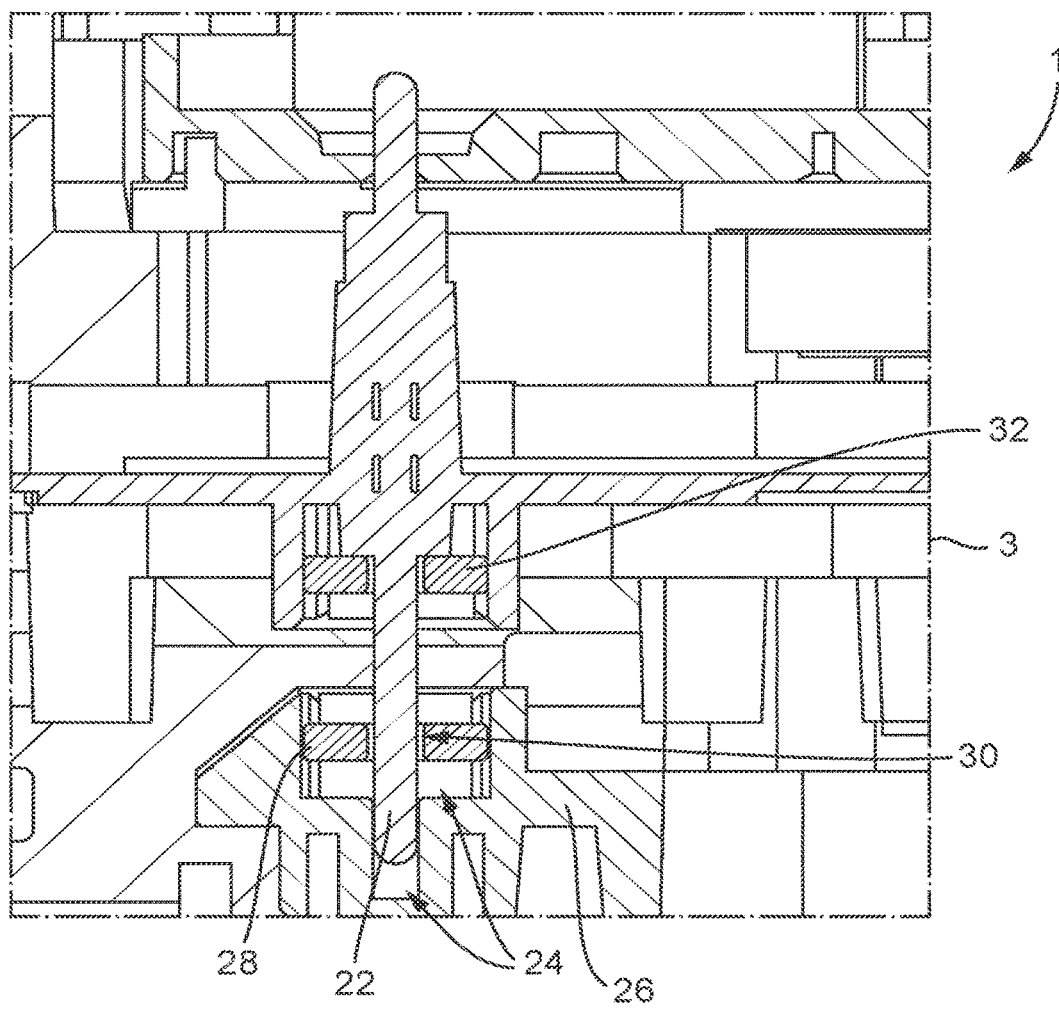
FIG. 8 shows a preferred embodiment of a fan according to the invention, including a "floating suspension" arrangement.

FIG. 8 shows a preferred embodiment of the fan, further including a "floating bearing" for reducing friction when the rotor rotates. Fan 1 (as e.g. depicted in FIG. 7) further includes first and second permanent suspension magnets 28, 32. The rotor 3 comprises a rotation shaft 22, an end of which is suspended in an opening 24 of a support structure 26 of the fan 1.

The first suspension magnet 28 is arranged in and fixed to the opening 24 of the support structure 26. The first suspension magnet 28 surrounds the rotation shaft 22 such that the rotation shaft 22 can freely rotate in an opening 30 of the first suspension magnet 28.

The second suspension magnet 32 is arranged at a distance from the first suspension magnet 28. The second suspension magnet 32 surrounds the rotation shaft 22 and is fixed to the rotation shaft 22 such that the second suspension magnet 32 rotates together with the rotation shaft 22 when the rotor 3 is rotating. The first and second suspension magnets 28, 32 are configured to repel each other. This can e.g. be achieved when corresponding magnetic poles (e.g. north <-> north, or south <-> south) of the suspension magnets 28 respectively 32 face each other.

In this embodiment, the rotation shaft 22 levitates (floats) above the base (bottom) of the opening 24 in which it is suspended. This results in a reduction in friction and wear on components. For example, the levitating rotation shaft 22 reduces the contact between the shaft 22 and the bottom of the opening 24 compared to a non-levitating rotation shaft. The reduction in contact reduces physical wear on both the rotation shaft 22 and the opening 24 (e.g., the end of the rotation shaft "drilling a hole" into the bottom of the opening 24 over time is prevented). In this embodiment, contact between the end of the rotation shaft 22 and the bottom of the opening is avoided by the "floating arrangement"—enabled by the first and second suspension magnets 28 and 32 which repel each other.

Figure 9:
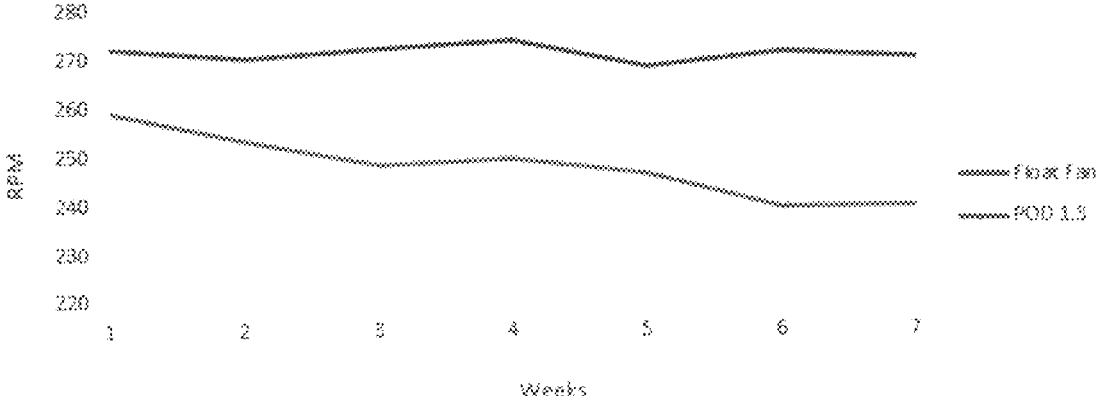
FIG. 9 shows the performance characteristics of a fan in accordance to the invention, compared to the performance characteristics of a fan not including suspension magnets.

FIG. 9 shows measurements of the "rounds per minute" (RPM) taken over time (over 7 weeks) for a fan according to FIG. 8 (upper graph, "Float Fan") compared to a fan not including the suspension magnets (lower graph, "POD 1.3"). It can clearly be seen that the fan according to the lower graph (i.e. not including the suspension magnets) is subject to more wear and tear over time such that its RPM value decreases over time. By contrast, the "Float Fan" according to FIG. 8 shows a much more favourable RPM behaviour over time which stays (almost) constant over the 7 week measuring period.

In the examples above, the magnetic element 16 is made of iron, the magnetic element 16 may also be made from cobalt or nickel.

In the example described with reference to FIG. 7, on the rotor 3 eight permanent magnets 14a, 14b, 14c, 14d, 14e, 14f, 14g and 14h are arranged on a circle 18 and spaced apart by 45 degrees. In other examples, on the rotor two, three, four, five, six, seven, nine, ten, eleven or twelve permanent magnets may be on a circle 18 in spaced apart arrangement.

It is envisaged that further modifications and developments can be made without departing from the scope of the invention described herein.

The invention claimed is:

1. A fan for an automatic dispensing device, wherein the fan is configured to generate an air flow when a rotor of the fan is rotating, the fan comprising:

a drive circuit;

an electromagnet having at least one electromagnetic coil, the electromagnetic coil connected to the drive circuit;

a rotor for generating the airflow; and at least four magnets arranged on a circle on the rotor and spaced apart by the same angle (alpha); and the electromagnetic coil of the electromagnet is arranged above or under the circle of the rotor and configured to attract or repel said magnets; and the drive circuit is configured to switch a current direction in the electromagnetic coil of the electromagnet to sequentially attract and then repel each magnet as the rotor rotates; and a magnetic element arranged above or under the rotor in proximity of the circle of the rotor wherein the magnetic element is configured to attract one of the magnets to its position when the electromagnetic coil is not powered by the drive circuit and the rotor is not rotating or gradually coming to a halt after the electromagnetic coil has been un-powered, wherein none of the other magnets assumes a position directly under or above the electromagnetic coil of the electromagnet when the rotor comes to a halt; and the rotor comprises a rotation shaft, an end of which is suspended in an opening of structure, the first suspension magnet surrounding the said rotation shaft such that the rotation shaft can freely rotate in an opening of the first suspension magnet; and, a second suspension magnet is arranged at a distance from the first suspension magnet, the second suspension magnet surrounding the rotation shaft and is fixed to the rotation shaft such that the second suspension magnet rotates together with the rotation shaft when the rotor is rotating; and the test and second suspension magnets are configured to repel each other.

2. The fan according to claim 1, wherein the magnetic element is metallic.

3. The fan according to claim 1, wherein the magnetic element is made of iron, cobalt or nickel.

4. The fan according to claim 1, wherein the magnetic element is a plate.

5. The fan according to claim 1, wherein the electromagnetic coil of the electromagnet and the magnetic element are spaced apart by at least 30 degrees relative to the circle.

6. The fan according to claim 1, wherein the fan comprises between four and twelve magnets.

7. The fan according to claim 1, wherein the electromagnetic coil of the electromagnet and the nearest magnet relative to the electromagnetic coil are spaced apart by an angle (beta) of between 5 and 45 degrees, relative to the circle when the electromagnetic coil is not powered by the drive circuit and the rotor is not rotating.

8. The fan according to claim 1, wherein the magnetic poles of each magnet are oriented in the same direction.

9. The fan of claim 8, wherein the drive circuit is configured to switch the direction of the current in the electromagnetic coil of the electromagnet as each magnet passes the electromagnet and when the electromagnet is equidistant from two adjacent magnets.

10. The fan according to claim 1, wherein the at least four magnets comprise one or more neodymium magnets.

11. The fan according to claim 1, wherein the fan is configured to be operated with the rotor rotating in a horizontal plane.

12. The fan according to claim 1, wherein the fan is powered by a solar panel.

13. The fan according to claim 5, wherein the electromagnetic coil of the electromagnet and the magnetic element are spaced apart by at least 45 degrees relative to the circle.

14. The fan according to claim 13, wherein the electromagnetic coil of the electromagnet and the magnetic element are spaced apart by at least 90 degrees relative to the circle.

15. The fan according to claim 6, wherein the fan comprises eight magnets.

16. The fan according to claim 7, wherein the electromagnetic coil of the electromagnet and the nearest magnet relative to the electromagnetic coil are spaced apart by an angle (beta) of between 5 and 25 degrees, relative to the circle when the electromagnetic coil is not powered by the drive circuit and the rotor is not rotating.

* * * * *